(12) United States Patent
Bode et al.

(10) Patent No.: US 7,633,078 B2
(45) Date of Patent: Dec. 15, 2009

(54) STORAGE PHOSPHOR LAYER AND SYSTEM AND METHOD FOR ERASING SAME

(75) Inventors: Andreas Bode, Munich (DE); Georg Reiser, Munich (DE); Marc Weber, Munich (DE); Ralph Thoma, Augsburg (DE); Stefan Stallmeister, Glonn (DE); Stephan Baunach, Munich (DE); Heike Minwegen, Bad Aibling (DE); Robert Fasbender, Erlangen (DE); Rupert Dedler, Jengen-Weinhauser (DE)

(73) Assignee: Agfa HealthCare NV, Mortsel (BE)

( * ) Notice: Subject to any disclaimer, the term of this patent is extended or adjusted under 35 U.S.C. 154(b) by 0 days.

(21) Appl. No.: 11/831,183

(22) Filed: Jul. 31, 2007

(65) Prior Publication Data

US 2008/0054200 A1    Mar. 6, 2008

(30) Foreign Application Priority Data

Aug. 31, 2006    (EP)    ................................ 06119938

(51) Int. Cl.
*G03C 5/16*    (2006.01)
(52) U.S. Cl. ..................................................... 250/588
(58) Field of Classification Search ................. 250/588
See application file for complete search history.

(56) References Cited

U.S. PATENT DOCUMENTS

| | | | |
|---|---|---|---|
| 4,742,225 A * | 5/1988 | Chan ........................... 250/586 |
| 4,752,687 A * | 6/1988 | Yamada ....................... 250/588 |
| 4,786,808 A | 11/1988 | Saito |
| 4,849,633 A | 7/1989 | Yamada et al. |
| 4,852,975 A * | 8/1989 | Yamada ....................... 250/588 |
| 4,882,489 A * | 11/1989 | Saotome et al. ............. 250/582 |
| 5,534,709 A | 7/1996 | Yoshimoto et al. |
| 5,905,014 A * | 5/1999 | Van de Bergh ............. 430/139 |
| 6,369,402 B1 | 4/2002 | Gebele et al. |
| 6,373,074 B1 | 4/2002 | Mueller et al. |

(Continued)

FOREIGN PATENT DOCUMENTS

EP    0 704 716 A1    4/1996

(Continued)

OTHER PUBLICATIONS

International Search Report from EP 06119938.6, filed on Aug. 31, 2006.

(Continued)

*Primary Examiner*—David P Porta
*Assistant Examiner*—Shun Lee
(74) *Attorney, Agent, or Firm*—Houston Eliseeva LLP

(57) ABSTRACT

An apparatus (1) for erasing a storage phosphor layer (2) includes a drive (5) for producing a relative movement between the storage phosphor layer (2) and the radiation source (8), the storage phosphor layer (2) lying or being moved in a holding plane (7), and a reflector (11) for reflecting radiation. The reflector (11) is arranged and designed to reflect erasing radiation reflected by the storage phosphor layer (2) in the direction of the storage phosphor layer (2). A width (14) of the reflector (11) in the direction (6) of the relative movement is at least ten times as great as a smallest distance (15) between the reflector (11) and the holding plane (7).

31 Claims, 3 Drawing Sheets

U.S. PATENT DOCUMENTS

| | | | |
|---|---|---|---|
| 6,528,812 B1 | 3/2003 | Leblans et al. | |
| 6,642,535 B2 | 11/2003 | Gebele et al. | |
| 6,762,882 B2 | 7/2004 | Melzer et al. | |
| 6,858,861 B2 | 2/2005 | Gebele | |
| 6,897,994 B2 | 5/2005 | Thoma et al. | |
| 7,071,484 B2 | 7/2006 | Lind et al. | |
| 7,075,200 B2 | 7/2006 | Minato et al. | |
| 7,109,496 B2 | 9/2006 | Gebele et al. | |
| 7,122,822 B2 | 10/2006 | Bode et al. | |
| 7,151,272 B2 | 12/2006 | Nitsche et al. | |
| 7,170,079 B2 | 1/2007 | Fasbender et al. | |
| 7,170,080 B2 | 1/2007 | Fasbender et al. | |
| 7,176,476 B2 | 2/2007 | Lind et al. | |
| 7,227,167 B2 | 6/2007 | Leblans et al. | |
| 2003/0123613 A1 | 7/2003 | Evans et al. | |
| 2004/0004843 A1 | 1/2004 | Melzer et al. | |
| 2004/0130768 A1 | 7/2004 | Thoma et al. | |
| 2004/0208639 A1 | 10/2004 | Melzer et al. | |
| 2004/0232365 A1 | 11/2004 | Reiser et al. | |
| 2004/0238765 A1 | 12/2004 | Bode et al. | |
| 2004/0239998 A1 | 12/2004 | Reiser | |
| 2005/0012057 A1 | 1/2005 | Smith et al. | |
| 2005/0017207 A1 | 1/2005 | Trzcinski et al. | |
| 2006/0022157 A1 | 2/2006 | Reiser | |
| 2006/0180773 A1 | 8/2006 | Frankenberger et al. | |
| 2006/0180777 A1 | 8/2006 | Frankenberger et al. | |
| 2007/0152179 A1 | 7/2007 | Mair et al. | |
| 2007/0153975 A1 | 7/2007 | Mair et al. | |
| 2008/0054201 A1* | 3/2008 | Bode et al. | 250/588 |
| 2008/0054202 A1* | 3/2008 | Bode et al. | 250/588 |

FOREIGN PATENT DOCUMENTS

| | | |
|---|---|---|
| EP | 0 964 270 A2 | 12/1999 |
| EP | 1 403 077 A1 | 3/2004 |
| EP | 1 403 695 A1 | 3/2004 |
| EP | 1 503 241 A1 | 2/2005 |
| JP | 2003-186128 | 7/2003 |
| JP | 2005-275075 | 10/2005 |
| WO | 01/50960 A2 | 7/2001 |

OTHER PUBLICATIONS

European Search Report from EP06119939.4, filed Aug. 31, 2006.
European Search Report from EP06125512.1, filed on Dec. 6, 2006.

* cited by examiner

STORAGE PHOSPHOR LAYER AND SYSTEM AND METHOD FOR ERASING SAME

RELATED APPLICATIONS

This application claims priority to European Patent Application No. EP06119938.6, filed on Aug. 31, 2006, which is incorporated herein by reference in its entirety.

This application relates to U.S. Application Publication No. US 2008/0054201 A1, published on Mar. 6, 2008, titled "Storage Phosphor Layer and System and Method for Erasing Same," by Dr. Andreas Bode et al., and U.S. Application Publication No. U.S. 2008/0054202 A1, published on Mar. 6, 2008, titled, "Storage Phosphor Layer and System and Method for Erasing Same," by Dr. Andreas Bode et al.

BACKGROUND OF THE INVENTION

Apparatuses for erasing a storage phosphor layer with a radiation source for producing and emitting erasing radiation are used in particular in the field of computer radiography (CR) for medical purposes.

The apparatuses are used to produce a picture of an object, for example a patient or a body part of the patient, by means of X-ray radiation. The picture is stored in a storage phosphor layer as a latent picture. Therefore, this type of X-ray picture contains X-ray information about the object. In order to read out the X-ray information stored in the storage phosphor layer, the storage phosphor layer is stimulated by means of an irradiation device. As a result of this stimulation the storage phosphor layer emits radiation, which has an intensity corresponding to the X-ray information stored in the storage phosphor layer. The radiation emitted by the storage phosphor layer is collected by a detection device and converted into electrical signals, which contain an image of the X-ray information. The electrical signals are further processed and the X-ray information stored in the storage phosphor layer is then made visible. The X-ray information can be displayed directly on a monitor, for example, or be written onto a photographic X-ray film by means of a printer used especially for X-ray pictures.

After reading out the X-ray information from the storage phosphor layer, remains of the latent picture remain in the latter. Furthermore, noise information can be stored in the layer. In order to be able to use the storage phosphor layer for further X-rays, it is important erase this information. For this procedure, a radiation source is used that emits erasing radiation onto the storage phosphor layer. An apparatus for erasing a storage phosphor layer is known from U.S. Pat. No. 7,075,200 B2. As a radiation source, this erasing apparatus contains two lines with light emitting diodes, disposed parallel to one another, for emitting the erasing radiation. For erasure, the storage phosphor layer is pushed in a direction of conveyance through a ray path of the lines of light emitting diodes. The two lines of light emitting diodes are integrated with reflectors which are spaced apart from one another. The reflectors serve to reflect erasing radiation emitted by the light emitting diodes in the direction of the storage phosphor layer. The reflectors have a groove-shaped cross-sectional surface with obtuse inner angles so that the groove-shaped profile of the reflectors opens from the light emitting diode arrangement in the direction of the storage phosphor layer. The width of the reflectors here in the direction of conveyance is adapted to their function of guiding the radiation of the erasing radiation emitted by the light emitting diodes.

SUMMARY OF THE INVENTION

The present invention relates to an apparatus for erasing a storage phosphor layer with a radiation source for producing and emitting erasing radiation, a drive for producing a relative movement between the storage phosphor layer and the radiation source, the storage phosphor layer lying or being moved in a holding plane, and a reflector for reflecting radiation. The present invention further relates to a system with this type of apparatus and a storage phosphor layer.

It is the object of the present invention to enable high efficiency when erasing a storage phosphor layer.

According to the invention, the reflector is arranged and designed to reflect erasing radiation reflected by the storage phosphor layer in the direction of the storage phosphor layer. For this, a width of the reflector in the direction of the relative movement is at least ten times as great as a smallest distance between the reflector and the holding plane.

The knowledge which forms the basis of the present invention is that the storage phosphor layer generally has a high degree of reflection. Due to this, a large part of the erasing radiation is reflected without being used or absorbed and does not contribute to the erasure of undesired picture information stored in the storage phosphor layer. Upon the basis of the present invention, the erasing radiation reflected by the storage phosphor layer is reflected back again by the reflector in the direction of the storage phosphor layer. This reflection can be directed (specular) or diffuse. The erasing radiation reflected back by the reflector can therefore also contribute to erasure of the storage phosphor layer. In this way the efficiency of the erasure is substantially improved. Furthermore, the power requirement is less, and this leads to less lost heat and an increase in lifespan. Furthermore, it can be presumed that the failure rate will be reduced. If appropriate, in this way one can dispense with cooling of the radiation source. This guarantees a cost-effective erasing apparatus. Furthermore, less space is often required. The design of the reflector can advantageously be adapted simply to the type and form of the storage phosphor layer. In particular, the reflector is arranged such that it includes at least one reflection surface, which faces towards the holding plane. By means of the dimensioning of the reflector with its large width in the direction of the relative movement and its distance from the holding plane for the storage phosphor layer, it can in particular be guaranteed that a large part of the erasing radiation reflected or dispersed by the storage phosphor layer can be collected and reflected back again in the direction of the storage phosphor layer.

In one advantageous embodiment of the invention, the reflector has a flat reflector surface which extends parallel to the holding plane. This type of reflector form can reliably reflect reflected erasing radiation back to the storage phosphor layer. This form of reflector can be manufactured cheaply and can be compact in design.

In a further advantageous embodiment the reflector has a reflector surface with a structure. With this type of structure the efficiency of the erasure can be even further increased. The structure can in particular be fluted, or in the form of a roof or saw teeth, triangular or other similar shape.

In one particularly preferred embodiment of the invention, the structured reflector surface is retroreflective in form so that it reflects back at least part of the erasing radiation dispersed back by the storage phosphor layer to the same points of the storage phosphor layer. This type of retroreflective reflector surface guarantees particularly efficient erasure of the storage phosphor layer. At those points which have reflected a lot of erasing radiation, a lot of erasing radiation is also reflected back. The retroreflective reflector surface can in particular be designed in the form of a so-called "cat's eye", and be inserted for example as a film. This is particularly space saving and cost-effective.

Particularly advantageously, the reflector has at least two reflector surfaces so that the reflector, considered in the direction of the relative movement, is formed to either side of the radiation source. In this way a particularly large amount of erasing radiation can be collected and reflected back.

Preferably, the reflector has a groove- or trough-shaped cross-sectional surface. This type of reflector is particularly easy to produce and achieves a high level of efficiency when erasing.

It is particularly preferable for the groove- or trough-shaped cross-sectional surface to have obtuse inner angles which are in particular greater than or equal to 130°. In this way the quantity of reflected erasing radiation which is reflected back to the storage phosphor layer, is increased even further.

In one advantageous embodiment of the invention, considered in the direction of the relative movement, reflector extension surfaces extending parallel to the holding plane adjoin both ends of the groove. Preferably, the reflector extension surfaces have structures. These embodiments respectively guarantee even better efficiency of the erasure process.

In a further advantageous embodiment the reflector has reflecting layers on reflector surfaces facing towards the holding plane. In this way the degree of reflection can be perceptibly improved.

In one particularly preferred embodiment of the invention, the reflector is formed with mirror- or reflection-symmetry in the direction of the relative movement, an axis of symmetry extending at right angles to the direction of the relative movement, and considered in the direction of the relative movement, centrally through the radiation source. By means of this type of reflector a large quantity of reflected erasing radiation can be collected to both sides of the radiation source and be reflected back to the storage phosphor layer.

Particularly advantageously, the radiation source has at least two lines with light emitting diodes extending at right angles to the direction of the relative movement and parallel to the holding plane. In this way a sufficiently high intensity of erasing radiation can be produced, the power consumption of the light emitting diodes being particularly low.

Preferably, the at least two lines with light emitting diodes are integrated into the reflector. The distance between the at least two lines and/or the distance between the individual light emitting diodes within the respective line is smaller than or equal to a distance between the light emitting diodes and the holding plane. Due to this, the reflector, and so also the erasing apparatus, can be particularly compact in design. Furthermore, the erasing radiation emitted by the individual light emitting diodes is emitted, particularly well mixed, onto the storage phosphor layer.

Particularly preferably, a particular reflector is allocated to each of the at least two lines with light emitting diodes. The light emitting diodes of the respective lines further emit radiation, in particular in a narrow-band wavelength range different to that of the light emitting diodes of the other lines. The reflectors are designed in particular so that they contribute to separation of the erasing radiation with the different wavelength ranges emitted by the different lines of light emitting diodes. In this way particular spectral ranges can be prevented from mutually affecting or disrupting one another. The wavelength ranges can advantageously be chosen such that wavelengths which do not contribute to the erasure of the type of storage phosphor layer used are not available. Due to this, the filtering out of these wavelengths, which would otherwise be necessary, is not necessary. Furthermore, particularly good erasing efficiency is achieved.

Preferably, the at least two lines with light emitting diodes are disposed one behind the other in the direction of the relative movement such that when implementing the relative movement in order to erase the storage phosphor layer, shortwave erasing radiation hits the storage phosphor layer before longwave erasing radiation. In particular here, blue erasing radiation can be directed at the storage phosphor layer before red erasing radiation. In this way particularly good erasing efficiency is guaranteed.

Preferably, an intensity of the longwave erasing radiation is greater than an intensity of the shortwave erasing radiation. In particular, a ratio of blue to red erasing radiation can be chosen such that 66% of the erasing radiation is red and 33% of the erasing radiation is blue erasing radiation. This relationship guarantees even better erasing efficiency.

Particularly preferably, a further reflecting surface positioned opposite the reflector, as considered in the direction at right angles to the direction of the relative movement, is provided for reflecting erasing radiation. The further reflecting surface can be formed such that it reflects the erasing radiation directionally or diffusely. Advantageously, by means of this further reflecting surface, at the start and/or at the end of the erasing process, i.e. when the ray path of the radiation source is not or not fully directed at the storage phosphor layer, the erasing radiation emitted by the radiation source can be reflected by the further reflecting surface in the direction of the reflector. The erasing radiation reflected by the further reflecting surface and which in particular has not yet reached the storage phosphor layer, can therefore be directed by the reflector towards the storage phosphor layer. In particular, the front and, if appropriate, the rear edge of the storage phosphor layer can therefore be erased with a high level of efficiency.

Preferably, the further reflecting surface is disposed on the side of the holding plane facing away from the reflector. In this way it can be particularly well guaranteed that erasing radiation not hitting the storage phosphor layer is reflected by the further reflecting surface so as to then be reflected by the reflector in the direction of the storage phosphor layer.

Particularly preferably, the further reflecting surface has a width in the direction of the relative movement which is at least as great as that of the reflector. In this way it can be guaranteed that forms of the further reflecting surface and of the reflector correspond particularly well to one another. A particularly large quantity of erasing radiation emitted by the radiation source can be reflected by the further reflecting surface, and a large quantity of this reflected erasing radiation is reflected by the reflector in the direction of the storage phosphor layer. In this way, a particularly high level of erasing efficiency can be achieved.

Preferably, the storage phosphor layer of the system according to the invention has a degree of reflection for the erasing radiation of greater than or equal to 70%, and in particular greater than or equal to 80%. The erasing apparatus according to the invention can be used particularly efficiently for storage phosphor layers with this high level of reflection.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
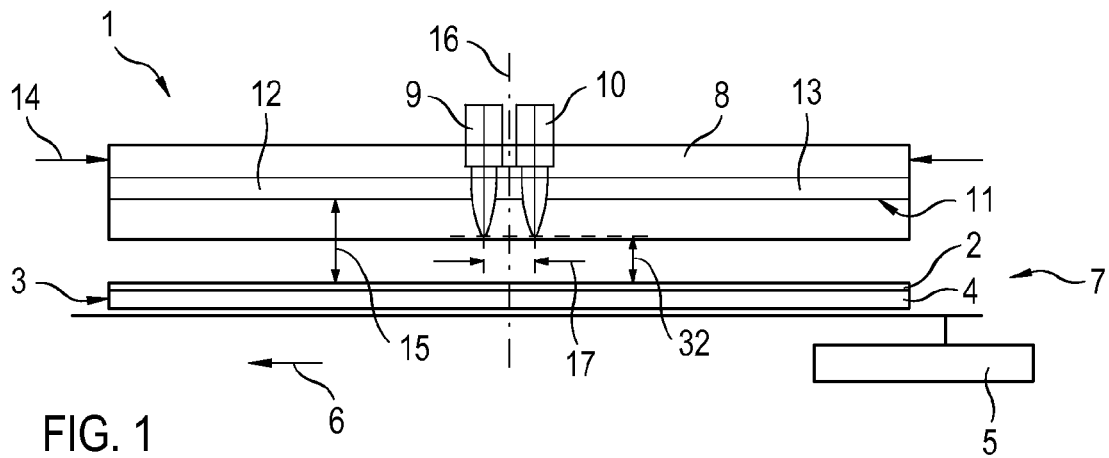
FIG. 1 shows a first exemplary embodiment of an erasing apparatus according to the invention with a reflector which has flat reflector surfaces extending parallel to a storage phosphor layer.

FIG. 1 shows a first exemplary embodiment of an erasing apparatus 1 that is constructed according to the principles of the present invention for erasing X-ray information which is stored in a storage phosphor layer 2 of a storage phosphor plate 3. The storage phosphor plate 3 has a carrying layer 4 on which the storage phosphor layer 2 is placed. The storage phosphor layer 2 is preferably made up of a plurality of phosphor particles that serve to store the X-ray information. Here, the carrying layer 4 is a laminate that is advantageously 1-2 millimeters (mm) thick. The storage phosphor plate 3 does not form part of the erasing apparatus 1, but is typically inserted into the erasing apparatus 1 from the outside. Within the erasing apparatus 1, the storage phosphor plate 3 is moved by means of a drive 5 in a direction of conveyance, which is represented by an arrow 6. The storage phosphor plate 3 is moved within the erasing apparatus 1 in a holding plane 7 and can be moved within this holding plane 7.

The erasing apparatus 1 comprises a radiation source 8 for emitting erasing radiation. The radiation source 8 here has two lines of light emitting diodes 9 and 10 disposed parallel to one another. The lines of light emitting diodes 9, 10 each contain a plurality of light emitting diodes disposed next to one another. The lines of light emitting diodes 9, 10 extend over the whole length of the storage phosphor layer 2. In the illustration according to FIG. 1 the length of the storage phosphor layer 2 extends at right angles to the direction of conveyance 6 and in the direction of the plane of the drawing sheet. The width of the storage phosphor layer 2 extends in the direction of conveyance 6. By means of the drive 5, the storage phosphor layer 2 is conveyed past the lines of light emitting diodes 9, 10 with even conveyance speed in the direction of conveyance 6. In this way the storage phosphor layer 2 passes through the ray paths of the lines of light emitting diodes 9, 10. Alternatively, it is also possible to convey the radiation source instead of the storage phosphor plate 3, the storage phosphor plate 3 then not being moved in the erasing apparatus 1. In both cases, a relative movement is implemented between the radiation source 8 and the storage phosphor layer 2 lying in the holding plane 7, which here extends in the direction of the arrow 6.

When conveying the storage phosphor plate 3, the erasing light emitted by the light emitting diodes of the lines of light emitting diodes 9, 10 hits the storage phosphor layer 2. Part of the erasing light penetrates into the storage phosphor layer 2 and erases the X-ray information remaining in the latter following a read-out and, if applicable, any noise that is present. Since the storage phosphor layer 2 has a degree of reflection of at least 70%, and in particular of at least 80% for the erasing light, a large part of the erasing light is reflected by the storage phosphor layer 2, without contributing to the erasure.

In order to achieve a high level of efficiency and a high degree of effectiveness when erasing, the erasing apparatus 1 according to the invention has a reflector 11. In the present exemplary embodiment the reflector 11 has two level reflector surfaces 12 and 13 extending parallel to the storage phosphor layer 2. Considered in the direction of conveyance 6, the reflector surfaces 12, 13 are disposed to either side of the radiation source 8 and are advantageously equal in size. However, it is also possible to provide just a single reflector surface on one of the sides of the radiation source 8. Furthermore, it is possible to design the reflector surfaces 12, 13 as one part, or one of the two being smaller than the other. The reflector 11 extends over the whole length of the storage phosphor layer 2 and, considered in the direction of conveyance 6, over a width 14. The reflector's smallest distance 15 is that from the surface of the storage phosphor layer 2 located in the holding plane 7. The width 14 is at least ten times greater than the smallest distance 15. The reflector 11 is mirror-symmetrical in form in the direction of conveyance 6. Here, an axis of symmetry 16 extends at right angles to the direction of conveyance 6, and in relation to the width 14, centrally through the radiation source 8. In the present exemplary embodiment, the axis of symmetry 16 therefore extends between the two lines of light emitting diodes 9, 10. The two lines of light emitting diodes 9, 10 are integrated centrally into the reflector 11 here. A distance 17 between the two lines of light emitting diodes 9, 10 is advantageously smaller than or equal to a distance 32 between the light emitting diodes and the storage phosphor layer 2 lying in the holding plane 7. On their surfaces facing towards the storage phosphor layer 2, the reflector surfaces 12, 13 have reflecting layers that are highly reflective for erasing light reflected by the storage phosphor layer 2. By means of the reflector 11, erasing light that is reflected or dispersed by the storage phosphor layer 2 is reflected back in the direction of the storage phosphor layer 2. Due to this re-reflection it is possible for the erasing light to now penetrate into the storage phosphor layer 2 in order to erase the X-ray information.

Figure 2:
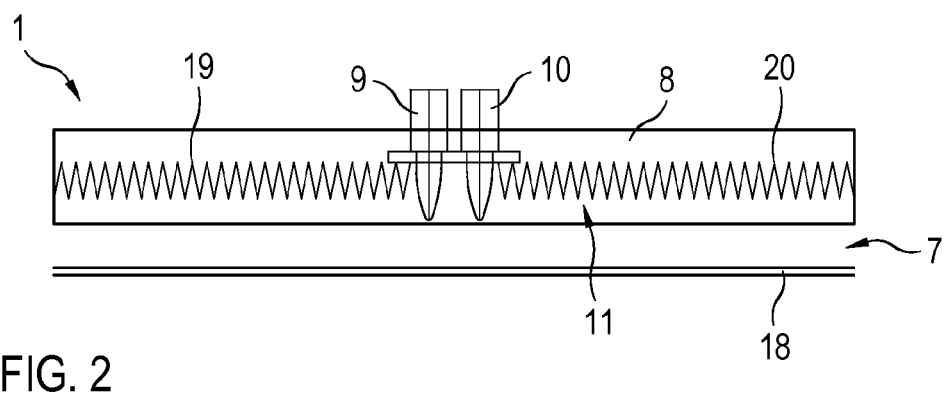
FIG. 2 shows a second exemplary embodiment of an erasing apparatus according to the invention with a reflector which has reflector surfaces with a triangular structure extending parallel to the storage phosphor layer.

FIG. 2 shows a second exemplary embodiment of the erasing apparatus 1 according to the invention. The storage phosphor plate is not shown here. A support 18 is shown over which the holding plane 7 for holding and moving the storage phosphor plate is located. The erasing apparatus 1 contains the reflector 11. Here, the latter has two reflector surfaces 19 and 20 which extend parallel to the holding plane 7 and the support 18. The reflector surfaces 19, 20 each have a structure which here is substantially triangular in form, similar to fine saw teeth. By means of this structure a retroreflective profile of the reflector surfaces 19, 20 is created.

Figure 3:
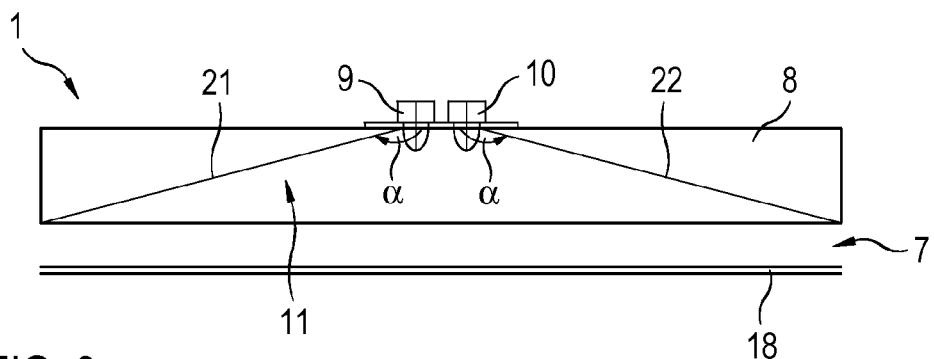
FIG. 3 shows a third exemplary embodiment of an erasing apparatus according to the invention with a groove-shaped reflector.

FIG. 3 shows a third exemplary embodiment of the erasing apparatus 1 according to the invention. In this third exemplary embodiment the reflector 11 is groove- or trough-shaped. Therefore, the cross-sectional surface of the reflector 11 is in the shape of a groove. For this, the reflector 11 has two reflector surfaces 21, 22 in a straight line that extend outwards at an angle from the radiation source 8 with obtuse inner angles α. The inner angles α here are approximately 165°.

Figure 4:
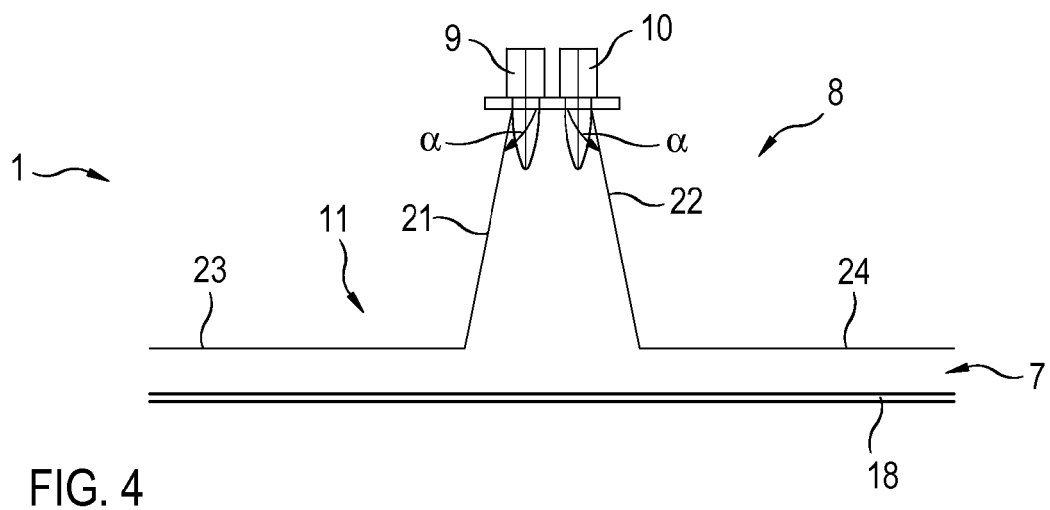
FIG. 4 shows a fourth exemplary embodiment of an erasing apparatus according to the invention with a groove-shaped reflector which has reflector extensions to the side extending from the ends of the groove and which extend evenly and parallel to the storage phosphor layer.

FIG. 4 shows a fourth exemplary embodiment of the erasing apparatus 1 according to the invention. Here, the reflector 11 is also formed in the shape of a groove by means of the two reflector surfaces 21, 22 in a straight line. The inner angles α of the groove-shaped cross-sectional surface are approx. 110° here. The reflector 11 has reflector extensions 23, 24 to the side extending from the lower ends of the groove that extend outwards evenly and parallel to the holding plane 7 for the storage phosphor plate.

Figure 5:
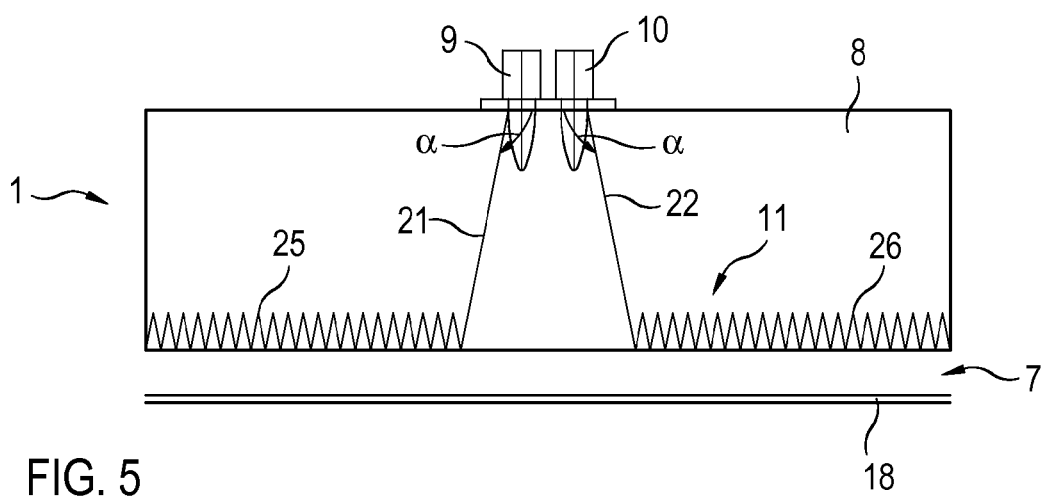
FIG. 5 shows a fifth exemplary embodiment of an erasing apparatus according to the invention with the groove-shaped reflector which has reflector extensions to the side extending from the ends of the groove and which extend parallel to the storage phosphor layer and have a fine triangular structure.

FIG. 5 shows a fifth exemplary embodiment of the erasing apparatus 1 according to the invention. Here, the reflector 11, like the reflector 11 according to the fourth exemplary embodiment, is formed in the shape of a groove by means of the two reflector surfaces 21, 22 in a straight line. The inner angles α of the groove-shaped cross-sectional surface are approximately 110°. The reflector 11 has reflector extensions 25, 26 to the side extending from the lower ends of the groove which extend outwards parallel to the holding plane 7 for the storage phosphor plate. Here, the reflector extensions 25, 26 to the side have a fine triangular structure. By means of this structure a retroreflective profile of the reflector extensions 25, 26 is created.

Figure 6:
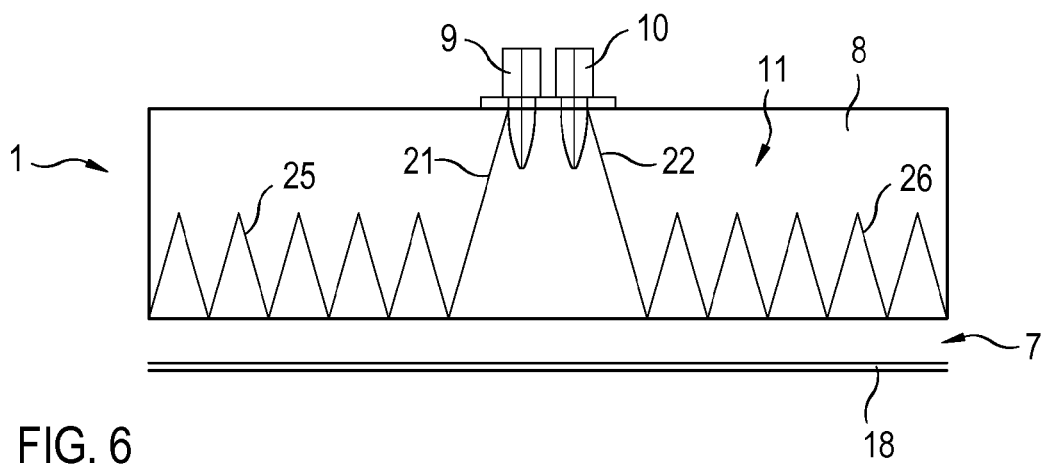
FIG. 6 shows a sixth exemplary embodiment of an erasing apparatus according to the invention with the groove-shaped reflector which has reflector extensions to the side extending from the ends of the groove, and which extend parallel to the storage phosphor layer and have a crude triangular structure.

FIG. 6 shows a sixth exemplary embodiment of an erasing apparatus 1 according to the invention. The reflector 11 here largely corresponds to the reflector of the erasing apparatus 1 according to the fifth exemplary embodiment according to FIG. 5. However, the side reflector extensions 25, 26 here have a crude or more coarse triangular structure. By means of this structure a retroreflective profile of the reflector extensions 25, 26 is also created.

Figure 7:
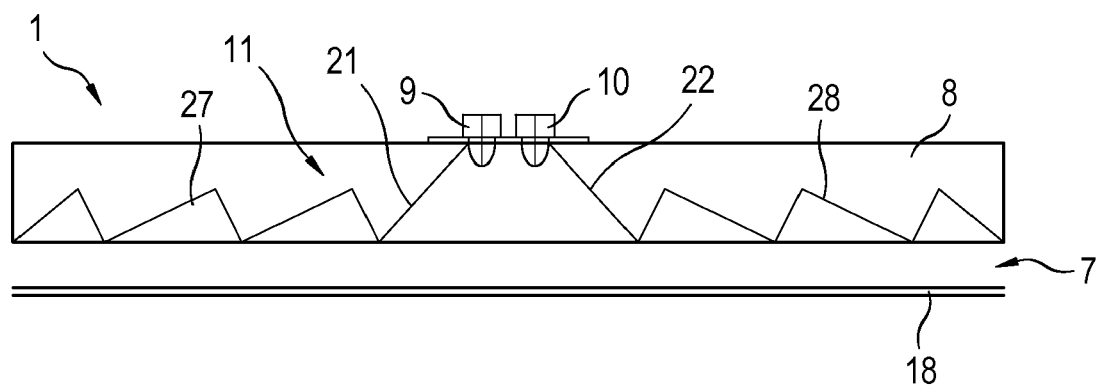
FIG. 7 shows a seventh exemplary embodiment of an erasing apparatus according to the invention with a reflector which has reflector extensions to the side extending from the ends of a small groove, and which extend parallel to the storage phosphor layer and have a saw-tooth shaped structure.

FIG. 7 shows a seventh exemplary embodiment of the erasing apparatus 1 according to the invention. Here, the reflector 11 is also formed in a groove shape by means of two reflector surfaces 21, 22 in a straight line. However, the reflector surfaces 21, 22 are shorter here than those of the exemplary embodiments according to FIGS. 4-6. The reflector 11 has reflector extensions 27, 28 to the side extending from the lower ends of the reflector surfaces 21, 22 of the groove and that extend outwards parallel to the holding plane 7 for the storage phosphor plate. Here, the side reflector extensions 27, 28 have a crude or coarse saw-tooth shaped structure with only a small number of saw teeth. By means of this structure a retroreflective profile of the reflector extensions 27, 28 is also created.

Figure 8:
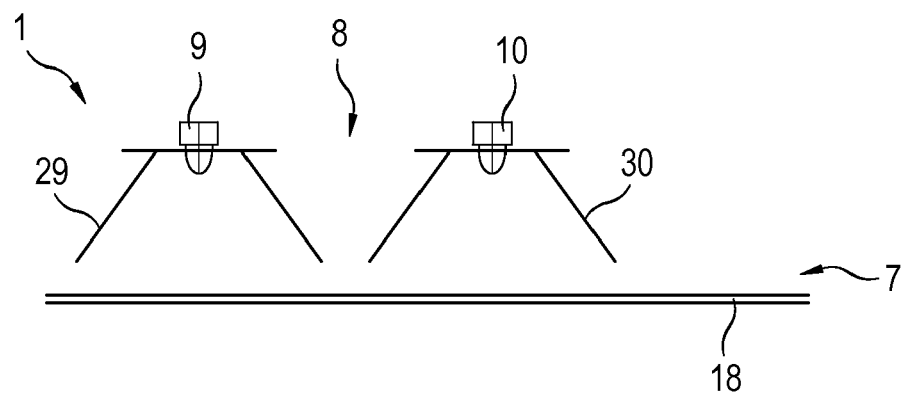
FIG. 8 shows an eighth exemplary embodiment of an erasing apparatus according to the invention with two lines of light emitting diodes which emit light in different wavelength ranges and which respectively have their own reflector.

FIG. 8 shows an eighth exemplary embodiment of the erasing apparatus 1 according to the invention. In this eighth exemplary embodiment the radiation source 8 contains the two lines of light emitting diodes 9, 10 which here, however, each have their own reflector. The line of light emitting diodes 9 is integrated into a trough-shaped reflector 29 and the line of light emitting diodes 10 into a trough-shaped reflector 30. The two reflectors 29, 30 are separated from one another so that the erasing light emitted by the lines of light emitting diodes 9, 10 hits the storage phosphor layer located in the erasing apparatus separately. The lines of light emitting diodes 9, 10 emit erasing light in different wavelength ranges. The line of light emitting diodes 9 emits erasing light in the blue wavelength range, and the line of light emitting diodes 10 in the red wavelength range. In this way good "color separation" and so a high level of erasing efficiency can advantageously be achieved. Therefore, in the direction of conveyance 6 of the storage phosphor plate first of all blue and then red erasing light hits the storage phosphor layer. Furthermore, the intensity of the longer wavelength or longwave, red erasing light is greater than the intensity of the shorter wavelength or shortwave, blue erasing light. The intensity portion of the red erasing light is advantageously approx. 66% here, and the intensity portion of the blue erasing light is approx. 33%.

In order to guarantee particularly efficient color separation, it can be advantageous for at least one of the reflectors 29 or 30 to be designed asymmetrically such that the flank of the respective reflector trough facing towards the respective other reflector 30 or 29 has an inner angle which is smaller than that of the flank facing away from the respective other reflector 30 and 29.

Figure 9:
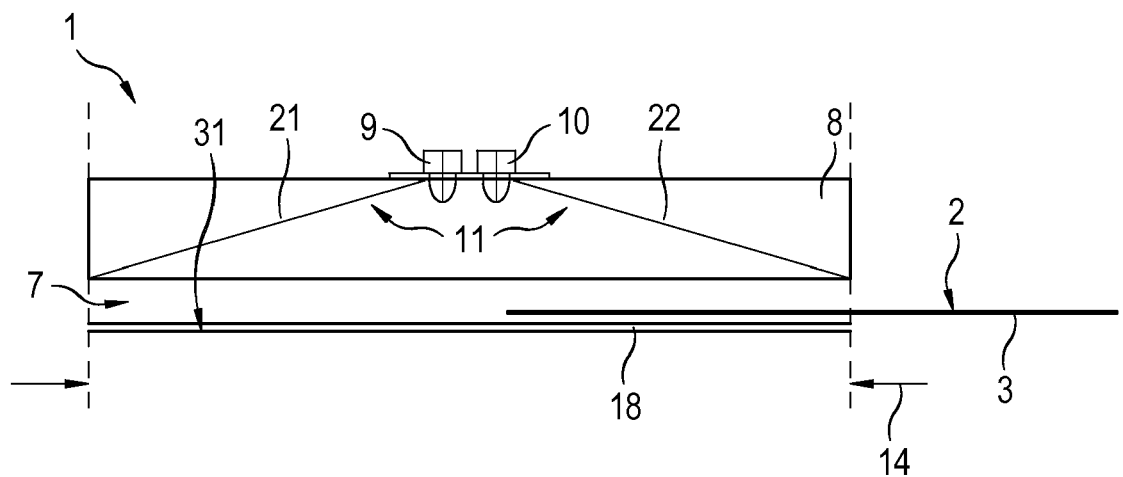
FIG. 9 shows the erasing apparatus according to the invention according to the third exemplary embodiment with a further reflection surface positioned opposite the reflector.

FIG. 9 shows the erasing apparatus 1 according to the invention according to the third exemplary embodiment according to FIG. 3. In the present exemplary embodiment, however, the erasing apparatus 1 has a further reflection surface 31 positioned opposite the reflector 11, as considered in the direction at right angles to the speed of conveyance 6. The reflection surface 31 is designed to reflect erasing light that has been emitted by the radiation source 8. If applicable, further erasing light reflected by the reflection surface 31 has been furthermore already reflected by the storage phosphor layer 2 and the reflector 11. In order to reflect erasing light, the reflection surface 31 is preferably placed on the side of the support 18 facing towards the radiation source 8, i.e. on the side of the holding plane 7 facing away from the reflector 11. The reflection surface 31 can advantageously be applied to the support 18 as a thin layer. The reflection surface 31 is therefore arranged such that the storage phosphor plate 3 is conveyed between the reflector 11 and the reflection surface 31. The reflection surface 31 reflects the erasing light to the reflector 11 directionally or diffusely. Here, the reflection surface 31 is advantageously as wide in the direction of conveyance 6 as the reflector 11. FIG. 9 shows the storage phosphor plate 3 inserted into the erasing apparatus 1. Advantageously, the reflection surface 31 guarantees that the erasing light emitted by the radiation source 8 then also contributes to the erasure with a high degree of effectiveness if the storage phosphor plate 3 is still not fully located within the erasing apparatus 1. In particular, it is guaranteed that the leading edge of the storage phosphor layer 2 is erased with increased efficiency. The same applies when the storage phosphor plate 3 is drawn out of the erasing apparatus 1. It is also the case with the exemplary embodiment according to FIG. 9 that for erasure of the storage phosphor layer 2 it is also possible to leave the storage phosphor plate 3 in the erasing apparatus 1 and to convey the radiation source 8 together with the reflector 11 and the reflection layer 31 positioned opposite along the storage phosphor plate 3.

In order to further improve the erasure efficiency, it is possible to provide additional optics on the radiation source 8, i.e. in particular on the lines of light emitting diodes 9, 10, which reduce the emission angle of the light emitting diodes. In this way the irradiated surface on the storage phosphor layer 2 can be narrower in form. This increases the power density for the erasure.

While this invention has been particularly shown and described with references to preferred embodiments thereof, it will be understood by those skilled in the art that various changes in form and details may be made therein without departing from the scope of the invention encompassed by the appended claims.

What is claimed is:

1. An apparatus for erasing a storage phosphor layer, comprising:
   a radiation source for producing and emitting erasing radiation,
   a drive for producing a relative movement between the storage phosphor layer and the radiation source, the storage phosphor layer lying or being moved in a holding plane,
   a reflector for reflecting erasing radiation reflected by the storage phosphor layer in the direction of the storage phosphor layer, a width of the reflector in the direction of the relative movement being at least ten times as great as a smallest distance between the reflector and the holding plane; and
   reflector extension surfaces on either side of the radiation source and adjoining both sides of the reflector, the reflector extension surfaces having structures creating a retroreflective profile.

2. The apparatus according to claim 1, wherein the reflector comprises a flat reflector surface that extends parallel to the holding plane.

3. The apparatus according to claim 1, wherein the reflector comprises a reflector surface with a structure.

4. The apparatus according to claim 1, wherein the reflector comprises at least two reflector surfaces, when considered in the direction of the relative movement, are on either side of the radiation source.

5. The apparatus according to claim 1, wherein the reflector has a groove- or trough-shaped cross-sectional surface.

6. The apparatus according to claim 5, wherein the groove- or trough-shaped cross-sectional surface has obtuse inner angles (α) which are in particular greater than or equal to 130°.

7. The apparatus according to claim 5, further comprising the reflector extension surfaces extending parallel to the holding plane and adjoining both ends of the groove.

8. The apparatus according to claim 1, wherein the reflector comprises reflecting layers on reflector surfaces facing towards the holding plane.

9. The apparatus according to claim 1, wherein the reflector is mirror-symmetric in the direction of the relative movement, an axis of symmetry extending at right angles to the direction of the relative movement, and, when considered in the direction of the relative movement, extends centrally through the radiation source.

10. The apparatus according to claim 1, wherein the radiation source comprises at least two lines with light emitting diodes extending at right angles to the direction of the relative movement and parallel to the holding plane.

11. The apparatus according to claim 10, wherein the at least two lines with light emitting diodes are integrated into the reflector and a distance between the at least two lines and/or a distance between the individual light emitting diodes within the respective lines is smaller than or equal to a distance between the light emitting diodes and the holding plane.

12. The apparatus according to claim 10, further comprising a reflector being allocated to each of the at least two lines with light emitting diodes, and the light emitting diodes of the respective lines emitting radiation in a narrow-band wavelength range, which is different from that of the light emitting diodes of the other lines.

13. The apparatus according to claim 12, wherein the at least two lines with light emitting diodes are disposed one behind the other in the direction of the relative movement and, when implementing the relative movement in order to erase the storage phosphor layer, shorter wavelength erasing radiation hits the storage phosphor layer before longer wavelength erasing radiation.

14. The apparatus according to claim 13, wherein an intensity of the longer wavelength erasing radiation is greater than an intensity of the shorter wavelength erasing radiation.

15. The apparatus according to claim 1, further comprising a further reflecting surface positioned opposite the reflector, as when considered in the direction at right angles to the direction of the relative movement, for reflecting erasing radiation.

16. The apparatus according to claim 15, wherein the further reflecting surface is disposed on the side of the holding plane facing away from the reflector.

17. The apparatus according to claim 15, wherein the further reflecting surface has a width in the direction of the relative movement that is at least as great as that of the reflector.

18. The apparatus according to claim 1, wherein the retroreflective profile is saw-toothed.

19. An apparatus for erasing a storage phosphor layer, comprising:
   a radiation source for producing and emitting erasing radiation,
   a drive for producing a relative movement between the storage phosphor layer and the radiation source, the storage phosphor layer lying or being moved in a holding plane,
   a reflector for reflecting erasing radiation reflected by the storage phosphor layer in the direction of the storage phosphor layer, a width of the reflector in the direction of the relative movement being at least ten times as great as a smallest distance between the reflector and the holding plane, wherein the reflector comprises a structured reflector surface that is retroreflective to reflect back at least part of the erasing radiation to points of the storage phosphor layer from which the radiation was previously reflected by the storage phosphor layer.

20. A system, comprising:
   a storage phosphor layer having a degree of reflection for the erasing radiation of greater than or equal to 70%; and
   an apparatus for erasing the storage phosphor layer, comprising:
   a radiation source for producing and emitting erasing radiation,
   a drive for producing a relative movement between the storage phosphor layer and the radiation source, the storage phosphor layer lying or being moved in a holding plane, a reflector for reflecting erasing radiation reflected by the storage phosphor layer in the direction of the storage phosphor layer, a width of the reflector in the direction of the relative movement being at least ten times as great as a smallest distance between the reflector and the holding plane; and reflector extension surfaces on either side of the radiation source and adjoining both sides of the reflector, the reflector extension surfaces having structures creating a retroreflective profile.

21. The system according to claim 20, wherein the storage phosphor layer has a degree of reflection for the erasing radiation of greater than or equal to 80%.

22. A method for erasing a storage phosphor layer, comprising:

producing and emitting erasing radiation toward the storage phosphor layer;

producing a relative movement between the storage phosphor layer and a radiation source producing the erasing radiation, the storage phosphor layer lying or being moved in a holding plane, and reflecting erasing radiation that was reflected by the storage phosphor layer in the direction of the storage phosphor layer using a reflector having a width in the direction of the relative movement being at least ten times as great as a smallest distance between the reflector and the holding plane; and further reflecting erasing radiation that was reflected by the storage phosphor layer in the direction of the storage phosphor layer using reflector extension surfaces on either side of the radiation source and adjoining both sides of the reflector, the reflector extension surfaces having structures creating a retroreflective profile.

23. The method according to claim 22, wherein the reflector comprises a flat reflector surface that extends parallel to the holding plane.

24. The method according to claim 22, wherein the reflector comprises a reflector surface with a structure.

25. The method according to claim 24, wherein the structured reflector surface is retroreflective to reflect back at least part of the erasing radiation to points of the storage phosphor layer from which the radiation was previously reflected by the storage phosphor layer.

26. The method according to claim 22, wherein the reflector comprises at least two reflector surfaces, when considered in the direction of the relative movement, are on either side of the radiation source.

27. The method according to claim 22, wherein the reflector has a groove- or trough-shaped cross-sectional surface.

28. The method according to claim 27, wherein the groove- or trough-shaped cross-sectional surface has obtuse inner angles ($\alpha$)which are in particular greater than or equal to 130°.

29. The method according to claim 28, wherein the reflector extension surfaces extend parallel to the holding plane and adjoin both ends of the groove.

30. The method according to claim 22, wherein the reflector comprises reflecting layers on reflector surfaces facing towards the holding plane.

31. The method according to claim 22, wherein the retroreflective profile is saw-toothed.

* * * * *